United States Patent
Savic et al.

(10) Patent No.: US 7,137,818 B2
(45) Date of Patent: Nov. 21, 2006

(54) DENTAL MOLDING, IN PARTICULAR AN ARTIFICIAL TOOTH

(75) Inventors: Novica Savic, Ranstadt (DE); Frank Uwe Stange, Langenargen (DE)

(73) Assignee: Heraeus Kulzer GmbH & Co.KG, Hanau (DE)

( * ) Notice: Subject to any disclaimer, the term of this patent is extended or adjusted under 35 U.S.C. 154(b) by 325 days.

(21) Appl. No.: 10/692,053

(22) Filed: Oct. 23, 2003

(65) Prior Publication Data

US 2004/0137409 A1    Jul. 15, 2004

(30) Foreign Application Priority Data

Oct. 23, 2002    (DE) ................................ 102 49 518

(51) Int. Cl.
*A61C 13/08*    (2006.01)

(52) U.S. Cl. ................ 433/202.1; 433/212.1; 433/222.1

(58) Field of Classification Search ............ 433/202.1, 433/212.1, 218, 222.1
See application file for complete search history.

(56) References Cited

U.S. PATENT DOCUMENTS

| | | | | |
|---|---|---|---|---|
| 2,377,382 A | * | 6/1945 | Slack, Jr. ............... | 252/301.35 |
| 2,895,050 A | | 7/1959 | Lee et al. .................. | 250/71 |
| 3,991,008 A | * | 11/1976 | Temin et al. ............... | 523/115 |
| 4,170,823 A | | 10/1979 | Smyth et al. ............... | 32/8 |
| 4,433,959 A | | 2/1984 | Faunce ........................ | 433/201 |
| 4,645,455 A | | 2/1987 | Kosmos .................... | 433/203.1 |
| 5,653,791 A | * | 8/1997 | Panzera et al. .............. | 106/35 |
| 6,063,830 A | * | 5/2000 | Deguchi et al. ............ | 523/115 |

FOREIGN PATENT DOCUMENTS

| | | |
|---|---|---|
| DE | 39 06 673 A1 | 9/1990 |
| DE | 19754 442 A1 | 6/1998 |
| EP | 1 226 807 A1 | 7/2002 |
| GB | 1143502 | 2/1966 |

OTHER PUBLICATIONS

European Search Report dated Jan. 30, 2004, EP 0302 2430.

* cited by examiner

*Primary Examiner*—Ralph A. Lewis
(74) *Attorney, Agent, or Firm*—Norris McLaughlin & Marcus PA

(57) ABSTRACT

A dental molding, in particular an artificial tooth, having an outer incisal layer and a dentin layer beneath that, characterized in that a layer of fluorescent material is provided between the dentin layer and the incisal layer. A method of producing the dental molding, and a method of using the dental molding to provide a patient with a more aesthetic appearance are also disclosed.

11 Claims, 1 Drawing Sheet

DENTAL MOLDING, IN PARTICULAR AN ARTIFICIAL TOOTH

This invention relates to a dental molding, in particular an artificial tooth, a method of producing this molding and a use thereof.

Natural teeth have a relatively high degree of fluorescence. This luminosity is strongly visible in so-called black light in particular. When artificial teeth are placed beside a natural tooth, the former are seen to have a much lower luminosity under certain lighting conditions and therefore appear unnatural.

The customary practice has been to add fluorescent agents to the particular material mixtures of the external incisal layer to then shape the tooth. The fluorescent agents improve the natural appearance of the tooth.

U.S. Pat. No. 4,170,823 discloses an artificial ceramic tooth, which contains a combination of terbium and cerium salts to produce the desired fluorescence. German Patent DE 197 54 442 A1 discloses a dental molding, in particular an artificial tooth, having an external incisal layer and a layer of dentin beneath that. Both layers may contain fluorescent substances. German Patent DE 39 06 673 A1 describes a ceramic dental molding in which an intermediate layer consisting of light-reflecting particles is applied to the basic composition. However, this layer is not fluorescent and is not situated between the dentin composition and the incisal composition.

Despite a variety of efforts, in many cases the resulting appearance does not meet today's high aesthetic demands.

Therefore, the problem on which the present invention is based is to provide a dental molding, in particular an artificial tooth, which will impart a much more natural appearance with regard to its fluorescence.

This problem is solved by a dental molding, in particular an artificial tooth, having an outer incisal layer and a dentin layer beneath it, wherein a layer of fluorescent material is provided between the dentin layer and the incisal layer. The inventive dental molding is produced by arranging at least one layer of fluorescent material between the dentin layer and the incisal layer. The inventive dental molding is useful in a process of providing a user with a more aesthetic appearance which involves fixing the inventive dental molding into the mouth (jaw bone) of said user.

With the inventive dental molding, in particular an artificial tooth, having an external incisal layer and a layer of dentin beneath that, a layer of fluorescent material is provided between the layer of dentin and the incisal layer. It is completely surprising that this structure makes a significant contribution toward imparting an extremely natural appearance of such teeth, in particular artificial teeth.

In addition, this even has a positive effect on the color of the inventive artificial teeth.

Furthermore, it is also possible to design the layer of fluorescent material so that it does not have a uniform thickness in order to achieve a certain irregularity and thus improve the natural appearance due to the fact that the fluorescence is not completely uniform (a natural tooth also does not have a uniform fluorescence).

Finally, the fluorescent agents present in the layer of fluorescent material are mechanically and chemically protected by the incisal layer (enamel layer) arranged above it to ensure a much longer-lasting effect on the one hand and better tolerability for the patient on the other hand.

In practice, the following embodiments have proven advantageous in particular with regard to the fluorescent effect and processability.

In the case of the dental molding, the layer of fluorescent material is composed of 5.00–95 percent by weight monomer, 0.5–90 percent by weight crosslinking agent, 0.1–1 percent by weight initiator and 0.01–30 percent by weight additive; in particular, the layer of fluorescent material contains up to 40 percent by weight bead polymer and/or up to 2 percent by weight pigment.

The monomer is at least one of those from the following group: ethylenically unsaturated monomers, monofunctional or polyfunctional acrylates and methacrylates, alkyl methacrylates, methyl methacrylate, ethyl methacrylate, isobutyl and n-butyl methacrylate, n-hexyl methacrylate, ethylhexyl methacrylate, hydroxyethyl methacrylate.

The crosslinking agent is at least one of those from the following group: polyfunctional methacrylates and polyfunctional acrylates, tetraethylene glycol dimethacrylate, triethylene glycol dimethacrylate, diethylene glycol dimethacrylate, ethylene glycol dimethacrylate, polyethylene glycol dimethacrylate, butanediol dimethacrylate, hexanediol dimethacrylate, decanediol dimethacrylate and dodecanediol dimethacrylate, bis-GMA, bis-GA, trimethylolpropane trimethacrylate, products of the reaction of isocyanates, diisocyanates or triisocyanates with hydroxymethacrylates or hydroxyacrylates or pentaerythritol tetraacrylates.

The bead polymer may be at least one of those from the following group: consisting of polymethyl methacrylate or copolymers with a particle size of 5 to 70 μm and a number average molecular weight between 400,000 and 900,000 (g/mol), wherein the copolymer is allyl methacrylate, ethyl methacrylate, ethylhexyl methacrylate, methyl acrylate, methacrylic acid, isobutyl and n-butyl methacrylate, hexyl methacrylate, butanediol dimethacrylate, ethylene glycol dimethacrylate.

The initiator may be at least one of those from the following group: peroxides, dibenzoyl peroxide, tertiary amines or dimethyl p-toluidine, where the amines may function as co-initiators in an amount of up to 0.5 percent by weight.

The pigment may be at least one of those from the following group: titanium dioxide, chromium oxides, antimony oxides, iron oxides, carbon, barium sulfate, azo calcium salts, nickel oxides, azo compounds, ultramarine and mixed oxides of these metals.

The additive may be at least one of those from the following group: fluorescent pigments and/or dyes: benzoid and quinoid aromatics and heteroaromatics, triaryl methanes, anthraquinones, chromenes, xanthenes, indoles, quinolines, acridines, phenoxazines, phenothiazines, azo dyes and stilbene dyes, indigo derivatives, phthalocyanines, tetrapyrrole dyes; optical brighteners: thiophenediyl benzoxazoles, stilbene benzoxazoles, 7-amino-4-methyl coumarin, dibenzopyridine, azaanthracene, phenylenediamine, naphthylamine, coumarin, 7-hydroxycoumarin; fillers: pyrogenic silicon dioxide, highly dispersed titanium dioxide with a particle size of less than 100 nm.

Finally, it is advantageous if the particle size of the fillers is approximately 10 nm, because an especially intense opalescence is achieved, yielding especially high-quality results aesthetically in individual cases.

In the inventive method for producing a dental molding, in particular an artificial tooth, in particular an inventive artificial tooth, a layer of fluorescent material is applied between the layer of dentin and the incisal layer, e.g., by spraying or painting a monomer liquid containing fluorescent particles on the inside of the incisal layer before applying the dentin layer, and finally the inner neck layer (the artificial tooth is constructed layer by layer from the outside to the inside more or less in a corresponding negative mold).

BRIEF DESCRIPTION OF THE DRAWING

This invention is explained in greater detail below on the basis of a drawing and one exemplary embodiment.

The drawing shows:

Figure 1:
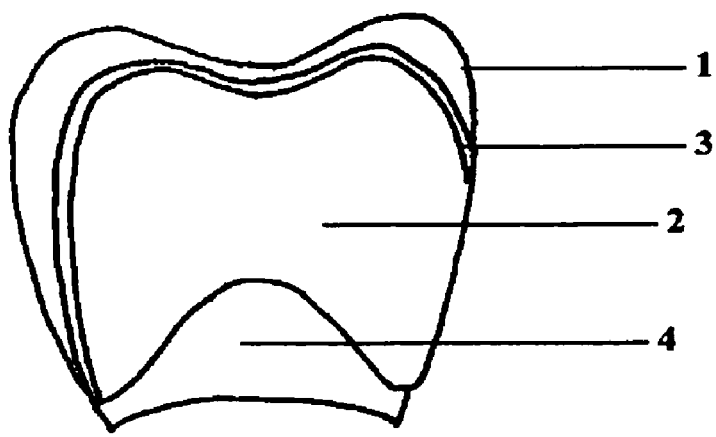
FIG. 1—a sketch of a cross-sectional diagram of a tooth.

A tooth having the inventive layer structure is shown in cross section in the diagram in FIG. 1. A dentin layer 2 is provided on an inner neck layer 4 and is in turn surrounded essentially completely by an outer incisal layer (enamel layer) 1. A fluorescent intermediate layer 3 is provided between the incisal layer (enamel layer) 1 and the dentin layer 2.

An artificial tooth is produced with a corresponding sequence of layers in multiple-part metal molds. The layer-by-layer construction begins with the incisal layer (enamel layer), with each layer being applied to the previous layer and polymerized separately.

Incisal Layer (Enamel Layer)

A conventional dental material consisting of crosslinked PMMA (polymethyl methacrylate) is used; this mixture contains a small amount of pigment to allow a good color effect. The main pigment used is titanium dioxide.

Fluorescent/opalescent Intermediate Layer

| Sample formula 1: | | |
|---|---|---|
| Monomer | Methyl methacrylate | 36.16% |
| Crosslinking agent | Ethylene glycol dimethacrylate | 50% |
| Initiator | Benzoyl peroxide | 0.4% |
| | Dimethyl p-toluidine | 0.4% |
| Bead polymer | Copolymer containing ethylhexyl acrylate (e.g., polymer B611 from the Ineos company) | 13% |
| Additive | Lumilux blue LZ fluorescent agent | 0.04% |

This yields a fluorescent intermediate layer.

| Sample formula 2: | | |
|---|---|---|
| Monomer | Methyl methacrylate | 36.13% |
| Crosslinking agent | Ethylene glycol dimethacrylate | 50% |
| Initiator | Benzoyl peroxide | 0.4% |
| | Dimethyl p-toluidine | 0.4% |
| Bead polymer | Copolymer containing ethylhexyl acrylate (e.g., polymer B611 from the Ineos company) | 13% |
| Additive | Nanoparticle titanium dioxide, particle size 10 nm | 0.07% |

This yields an opalescent intermediate layer.

Production and Use of the Enamels

Monomer and crosslinking agent are placed first in the container and then the bead polymer is dissolved in them in a closed container while stirring. Then the additive is added and dispersed by stirring. In the case of additives having large particles, it is advisable to break them down separately in some crosslinking agent, e.g., by milling, before adding them.

Then the initiator components are added immediately before use. They are advantageously applied to the prepolymerized incisal layer (enamel layer) by using a paintbrush. The layer solidifies by venting and/or incipient polymerization, so the dentin layer can be applied subsequently with no problem.

Dentin Layer and Neck Layer

A conventional dental material consisting of crosslinked PMMA (polymethyl methacrylate) is used here, where the mixture definitely contains more pigments to achieve a good color effect. The dentin in particular serves as the color carrier medium within the tooth.

The invention claimed is:

1. An artificial tooth comprising:
    (a) an inner neck layer;
    (b) a dentin layer provided above said neck layer;
    (c) a fluorescent material layer provided above said dentin layer; and
    (d) an outer enamel layer provided above said fluorescent material layer;
    wherein said fluorescent material layer comprises a fluorescent material obtainable by polymerizing a polymerizable mixture comprising 5.00 to 95% by weight of monomer, 0.5 to 90% by weight crosslinking agent, 0.1 to 1% by weight initiator and 0.01 to 30% by weight of fluorescent additive.

2. The artificial tooth according to claim 1, wherein the polymerizable mixture further comprises up to 40 percent by weight bead polymer.

3. The artificial tooth according to claim 2, wherein the bead polymer is at least one member selected from the group consisting of polymethyl methacrylate or copolymers with a particle size of 5 to 70 μm and a molecular weight between 400,000 and 900,000, wherein the copolymer is ally methacrylate, ethyl methacrylate, ethylhexyl methacrylate, methyl acrylate, methacrylic acid, isobutyl and n-butyl methacrylate, hexyl methacrylate, butanediol dimethacrylate, ethylene glycol dimethacrylate.

4. The artificial tooth according to claim 1, wherein the polymerizable mixture further comprises up to 2 percent by weight pigment.

5. The artificial tooth according to claim 4, wherein the pigment is at least one member selected from the group consisting of titanium dioxide, chromium oxides, antimony oxides, iron oxides, carbon, barium sulfate, azo calcium salts, nickel oxides, azo compounds, ultramarine and mixed oxides of these metals.

6. The artificial tooth according to claim 1, wherein the polymerizable mixture comprises at least one monomer selected from the group consisting of ethylenically unsaturated monomers, monofunctional or polyfunctional acrylates and methacrylates, alkyl methacrylate, methyl methacrylate, ethyl methacrylate, isobutyl and n-butyl methacrylate, n-hexyl methacrylate, ethylhexyl methacrylate and hydroxyethyl methacrylate.

7. The artificial tooth according to claim 1, wherein the polymerizable mixture comprises at least one crosslinking agent selected from the group consisting of polyfunctional methacrylates and polyfunctional, acrylates, tetraethylene glycol dimethacrylate, triethylene glycol dimethacrylate, diethylene glycol dimethacrylate, ethylene glycol dimethacrylate, polyethylene glycol dimethacrylate, butanediol dimethacrylate, hexanediol dimethacrylate, decanediol dimethacrylate and dodecanediol dimethacrylate, bis-GMA, bis-GA, trimethylolpropane trimethacrylate, products of the reaction of isocyanates, diisocyanates or triisocyanates with hydroxymethacrylates or hydroxyacrylates, pentaerythritol tetraacrylates.

8. The artificial tooth according to claim 1, wherein the polymerizable mixture comprises at least one initiator selected from the group consisting of peroxides, dibenzoyl peroxide, tertiary amines, dimethyl p-toluidine.

9. The artificial tooth according to claim 1, wherein the polymerizable mixture comprises at least one additive selected from the group consisting of fluorescent pigments and/or dyes: benzoid and quinoid aromatics and heteroaromatics, triaryl methanes, anthraquinones, chromenes, xanthenes, indoles, quinolines, acridines, phenoxazines, phenothiazines, azo and stilbene dyes, indigo derivatives, phthalocyanines, tetrapyrrole dyes; optical brighteners: thiophenediyl benzoxazoles, stilbene benzoxazoles, 7-amino-4-methyl coumarin, dibenzopyridine, azaanthracenes, phenylenediamine, naphthylamine, coumarin, 7-hydroxycouniarin; and fillers: pyrogenic silicon dioxide, highly dispersed titanium dioxide with a particle size of less than 100 nm.

10. The artificial tooth according to claim 9, wherein the particle size of the fillers is approximately 10 nm.

11. A method of providing a patient with a more aesthetic appearance, said method comprising affixing an artificial tooth according to claim 1 to a jaw bone of said patient.

* * * * *

UNITED STATES PATENT AND TRADEMARK OFFICE
CERTIFICATE OF CORRECTION

PATENT NO.       : 7,137,818 B2                                                Page 1 of 1
APPLICATION NO.  : 10/692053
DATED            : November 21, 2006
INVENTOR(S)      : Savic et al.

It is certified that error appears in the above-identified patent and that said Letters Patent is hereby corrected as shown below:

Column 4, Line 38, "is ally" should read -- is allyl --

Column 4, Line 56, "alkyl methacrylate," should read -- alkyl methacrylates, --

Signed and Sealed this

Fourth Day of May, 2010

David J. Kappos
*Director of the United States Patent and Trademark Office*